United States Patent
Kershaw et al.

(10) Patent No.: US 8,637,072 B2
(45) Date of Patent: Jan. 28, 2014

(54) ANTIMICROBIAL WOUND DRESSING COMPRISING GEL-FORMING FIBERS AND SPECIFIC RATIO OF SILVER TO NITRATE

(75) Inventors: David Kershaw, Deeside (GB); Barry DeBoorder, Heswall (GB); Stephen John Law, Nuneaton (GB)

(73) Assignee: Convatec Technologies, Inc., Las Vegas, NV (US)

(*) Notice: Subject to any disclaimer, the term of this patent is extended or adjusted under 35 U.S.C. 154(b) by 535 days.

(21) Appl. No.: 12/406,316

(22) Filed: Mar. 18, 2009

(65) Prior Publication Data
US 2010/0015208 A1   Jan. 21, 2010

(30) Foreign Application Priority Data

Mar. 19, 2008  (GB) .................................. 0805162.5

(51) Int. Cl.
  A61K 9/70   (2006.01)
  A61K 33/38  (2006.01)
  A61L 15/18  (2006.01)

(52) U.S. Cl.
  USPC .......... 424/445; 424/447; 424/618; 427/2.31; 514/54; 514/57

(58) Field of Classification Search
  None
  See application file for complete search history.

(56) References Cited

U.S. PATENT DOCUMENTS

| 3,061,469 A | * | 10/1962 | Manowitz et al. | 442/107 |
| 4,655,758 A | * | 4/1987 | Ring et al. | 604/374 |
| 5,064,652 A | * | 11/1991 | Bay | 424/445 |
| 2003/0180346 A1 | * | 9/2003 | Woods | 424/446 |
| 2004/0241213 A1 | | 12/2004 | Bray | |
| 2004/0247652 A1 | * | 12/2004 | Sabesan | 424/443 |
| 2007/0042024 A1 | * | 2/2007 | Gladman et al. | 424/445 |
| 2007/0166399 A1 | | 7/2007 | Burton | |

FOREIGN PATENT DOCUMENTS

| WO | WO9312275 | | 6/1993 | |
| WO | WO9416746 | | 8/1994 | |
| WO | WO02/24240 A1 | | 3/2002 | |
| WO | WO 02/43743 | * | 6/2002 | ............ A61K 31/74 |
| WO | WO03/022317 A1 | | 3/2003 | |
| WO | WO2006/015317 A2 | | 2/2006 | |
| WO | WO2006/105669 A1 | | 10/2006 | |

OTHER PUBLICATIONS

Parikh, D. V., et al. Textile Res. J. (2005), 75(2); pp. 134-138.*

* cited by examiner

*Primary Examiner* — Kevin S Orwig
(74) *Attorney, Agent, or Firm* — Wilson, Sonsini, Goodrich & Rosati

(57) ABSTRACT

The present invention relates to wound dressings, in particular to an antibacterial wound dressing based on silvered gel-forming fabric and to a process for the manufacture of such a wound dressing.

9 Claims, 3 Drawing Sheets

ANTIMICROBIAL WOUND DRESSING COMPRISING GEL-FORMING FIBERS AND SPECIFIC RATIO OF SILVER TO NITRATE

The present invention relates to wound dressings, in particular to an antibacterial wound dressing based on silvered gel-forming fabric and to a process for the manufacture of such a wound dressing.

BACKGROUND OF THE INVENTION

It has been known for many years that silver is a useful antibacterial agent with broad-spectrum activity together with compatibility with mammalian tissue, and there have been many proposals to incorporate silver into wound dressings to obtain the advantage of the bactericidal properties of silver in a wound dressing. In addition, silver has been applied to fibrous material previously for non-wound dressing purposes, usually for the purpose of enhancing electrical conductivity. Silver has been applied to such fibers, which are generally not gel-forming, in a variety of ways some of which involve immersing the fibers into a silver solution but detail of the procedures used is often lacking.

Carboxymethyl cellulose, in particular carboxymethylated lyocell, has the ability to absorb a great deal of exudates or wound fluid and to form a gel on its surface. This property of the material has been found to be particularly advantageous in the formation of wound dressings that are both absorbent and gel-forming. The carboxymethylation of cellulose is described in WO93/12275 and the use of carboxymethyl cellulose for wound dressings is described in WO94/16746. Calcium (or sodium/calcium) alginate is another material useful in the formation of wound dressings, because of its absorbency and gelling capability. Gel-forming fibers for use in wound dressings are water-absorbent fibers which become moist and slippery or gelatinous upon the uptake of wound exudate and thus reduce the tendency for the fibers to adhere to the wound. The gel-forming fibers may also swell. Gel-forming fibers can be of the type which retain their structural integrity on absorption of exudate or can be of the type which lose their fibrous form and become a structureless gel or solution on absorption of exudate.

There have, however been particular problems with the use of silver in wound dressings because of the fact that silver compounds are light-sensitive and darken on exposure to light. This can result in the production of products which have an unattractive visual aspect, even if they are technically suitable for use as wound dressings.

There are three particular aspects of the darkening of silver compounds in light which need to be addressed when seeking to produce a commercially acceptable silvered wound dressing. One aspect is the actual color of the product, namely the desire to have a product having a color acceptable to the consumer. The second aspect is the desire to produce a product having a uniform appearance. The third aspect is the stability (shelf life) of the color of the dressing within its packaging.

In the past it has been proposed to apply silver to fibers by a process including the step of contacting the fibers with a solution containing silver ions under conditions which do not cause irreversible gelling of the fibers by contacting the fibers essentially simultaneously with an entire solution containing silver ions. Rapid immersion of the fibers in this way is said to provide a very uniform uptake of silver ions. Such a process is described in U.S. Publication No. 20040241213. However, the immersion takes place in an organic solvent to prevent irreversible gelling of the fibers. Not only might this limit the solvents that can be used, the use of organic solvents might raise environmental and cost issues. The production of fabric from silvered fibers limits the product forms available for use as wound dressings to certain types of fabrics.

In order to treat certain types of wounds, for example burns or surgical wounds, it is desirable to use a fabric, either woven or non-woven, in order to provide improved properties to the resulting dressing. Such properties can include wet tensile strength, flexibility, reduced brittleness and reduced shrinkage.

It would be advantageous to have available a process for applying silver to a fabric comprising gel-forming fibers rather than the prior art process for producing silvered fibers and then forming a fabric from them. The process would enable wound dressings with improved properties to be produced which would bring the benefits of silver to more types of wound. It would also be advantageous to have available a process that eliminates the use of an organic solvent in the application of silver.

Moreover, it would be advantageous to have available a process for producing a hydroentanged non-woven silvered fabric for use as a wound dressing and in particular one comprising hydroentanged carboxymethylcellulose fibers. One possible route to producing such a fabric would be to hydroentangle a cellulosic fabric which is then carboxymethylated and reacted with silver to give it antibacterial properties. Because the fabric is preformed it is not possible to randomize the fibers post treatment with silver. The process for reacting the fabric with silver therefore needs to give a uniform application of silver to the fabric.

Surprisingly, we have found that silver may be applied to a fabric made of gel-forming fibers by spraying the fabric with a silver solution.

The processes of the prior art shy away from spraying as the silver solution used to deliver silver ions to the fibers is an aqueous organic solution, especially an aqueous alcoholic solution such as a mixture of ethyl alcohol and water. The solvent is considered necessary to avoid irreversible gelling of the fibers. Generally, the spraying of alcoholic solutions is avoided because of flammability and toxicity issues and the problems they raise in ensuring the safety of the operatives engaged in the process.

Surprisingly, we have found that it is possible to reduce the level of solvent in the silver solution and even to eliminate it by spraying the fabric with an aqueous silver solution.

SUMMARY OF THE INVENTION

Accordingly the invention provides a process for producing a silvered wound dressing including the steps of:
  (i) forming a fabric comprising gel forming fibers and
  (ii) contacting the fabric with an aqueous solution containing silver ions by spraying the solution onto the fabric.

The invention also provides an antibacterial wound dressing derived from gel-forming fibers having silver ions linked thereto, the wound dressing comprising nitrate.

It is important that the volume of the solution applied to the fabric is adjusted so that essentially the correct dosage of silver is applied to each unit area of the fabric. It is also important not to overwet the fabric otherwise the fibers gel and fuse. It is particularly preferred for the volume of solution with which the fabric is contacted to be adjusted such that essentially all the liquid that is sprayed is taken up by the fabric leaving no free liquid on the surface of the fabric.

The desired dosage of silver present in a final product is from 0.5% to 8% based on the total weight of the finished product, more preferably 0.5% to 2%, most preferably 0.75 to 1.5%.

The fabric is preferably sprayed with a solution comprising silver ions and with a separate solution containing sodium chloride. More preferably, the fabric is first sprayed with the silver solution. The sodium chloride solution reduces discoloration of the fabric.

Preferably, the fabric is in the form of a roll, the spray is applied to both sides of the fabric in a reel to reel process. The two-sided application gives the advantage that the resulting product is not sided and may be used on the patient either way up.

In conventional liquid spray systems a stream of liquid is made to break up due to the turbulence of the flow pattern within the stream. The liquid breaks up into droplets. This break up is assisted and directed by a compressed air stream and the droplets have velocities in the region of 10 to 20 m per second. Because the process of the invention preferably sprays salt solutions the liquid flow rate must be fast enough to prevent the salt caking on the spray head and blocking it. However, there is a constraint on the amount of fluid that can be sprayed on to the fabric as too much and it will gel and lose integrity. Hence, to use a conventional spray system would require a fast line speed.

Ultrasonic atomization occurs when a thin film of liquid passes over a surface which is vibrating in a direction which is perpendicular to the surface. The liquid film absorbs some of the energy and starts to vibrate forming standing waves on the surface. These waves are known as capillary waves. If the amplitude of the capillary wave is increased then an amplitude is reached where the wave becomes unstable and collapses. As it does so droplets of liquid are ejected from the surface. These droplets have a velocity in the region of 0.24 to 0.37 m per second. The low velocity of the droplets means that they can be readily entrained in an air stream and deposited on a surface.

We have found that to give a uniformity of application or coating of the solution on the fabric in order to ideally achieve a uniform dosage of silver on the fabric, the jets used to spray the fabric are preferably of the type which produce a stream of droplets with low forward velocity. By low forward velocity is meant that the droplet falls close to the nozzle and has no appreciable trajectory from the nozzle. The spray droplets are urged downwards onto the fabric by a forced air curtain which directs the spray pattern across the width of the fabric. An ultrasonic spray head has been found to give minimal forward velocity. Preferably, the flow rate of solution applied to each spray head is from 10 ml per minute to 100 ml per minute depending on the line speed of the roll.

Preferably, the solution containing silver ions is a silver nitrate solution which comprises from 1% w/w to 10% w/w of silver nitrate in water, more preferably 2% to 7% w/w and most preferably 3% to 5% w/w. Preferably, the sodium chloride solution comprises from 3% to 15% w/w of sodium chloride in water, more preferably 5% to 10% w/w and most preferably 5% to 7% w/w.

After spraying, the fabric is preferably wound on to a roll and left to react so that exchange can occur with the chloride ions. Typically, the rest time is approximately 5 minutes to one hour at ambient temperature. Following this the wet fabric is preferably unwound and passed through a forced air drier to reduce the fabric water content from 120% to 80% w/w, down to 5% to 15% w/w. Optionally, the fabric can then be treated with UV light so that a uniform color is developed. The energy dissipated by the UV tubes is 3.6 $KJm^{-2}$ approximately.

The fabric to be treated is preferably a carboxymethylated hydro entangled non woven fabric since these fabrics provide a compromise between the high strength but low absorbency of woven fabrics and the high absorbency but low strength of needle punched non wovens. More preferably, the fabric is a non-woven, hydroentangled, cellulosic with a basis weight of approximately 55 gsm.

Preferably, the line speed at which the process operates is from 1 m per minute to 10 m per minute.

The wound dressing of the invention preferably has a weight to weight ratio of silver to nitrate in the dressing of from 0.5 to 4, more preferably of from 1 to 2 and most preferably of from 1.5 to 1.8.

DETAILED DESCRIPTION OF THE PREFERRED EMBODIMENTS

The invention will now be illustrated by the following examples which show particularly preferred embodiments of the invention.

EXAMPLE 1

Figure 1:
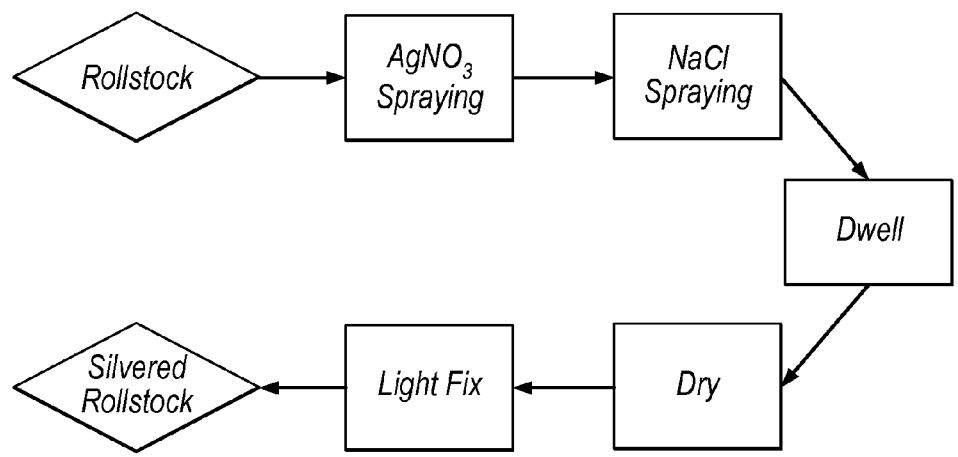
FIG. 1 is a flow chart of the steps used in one embodiment of the process of the invention.

The process of the invention was carried out using the process steps shown in FIG. 1.

Figure 2:
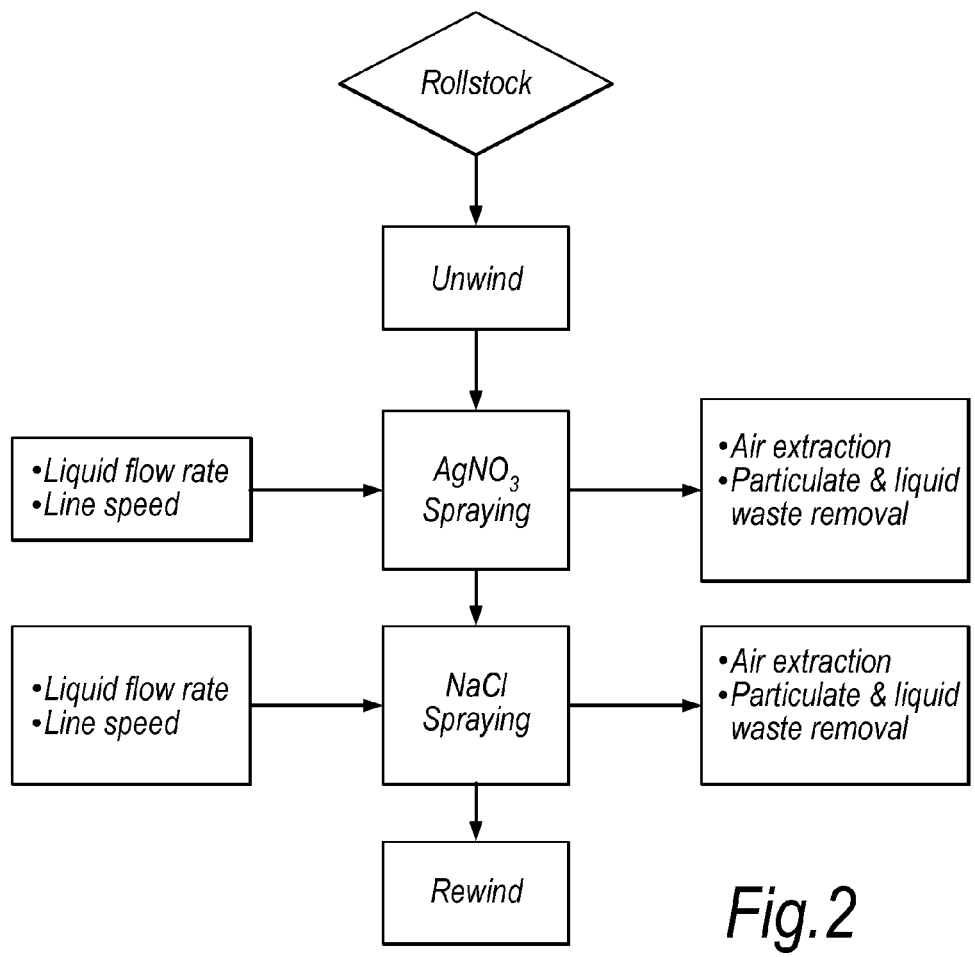
FIG. 2 is a flow chart of the spray step used in one embodiment of the process of the invention.
Figure 5:
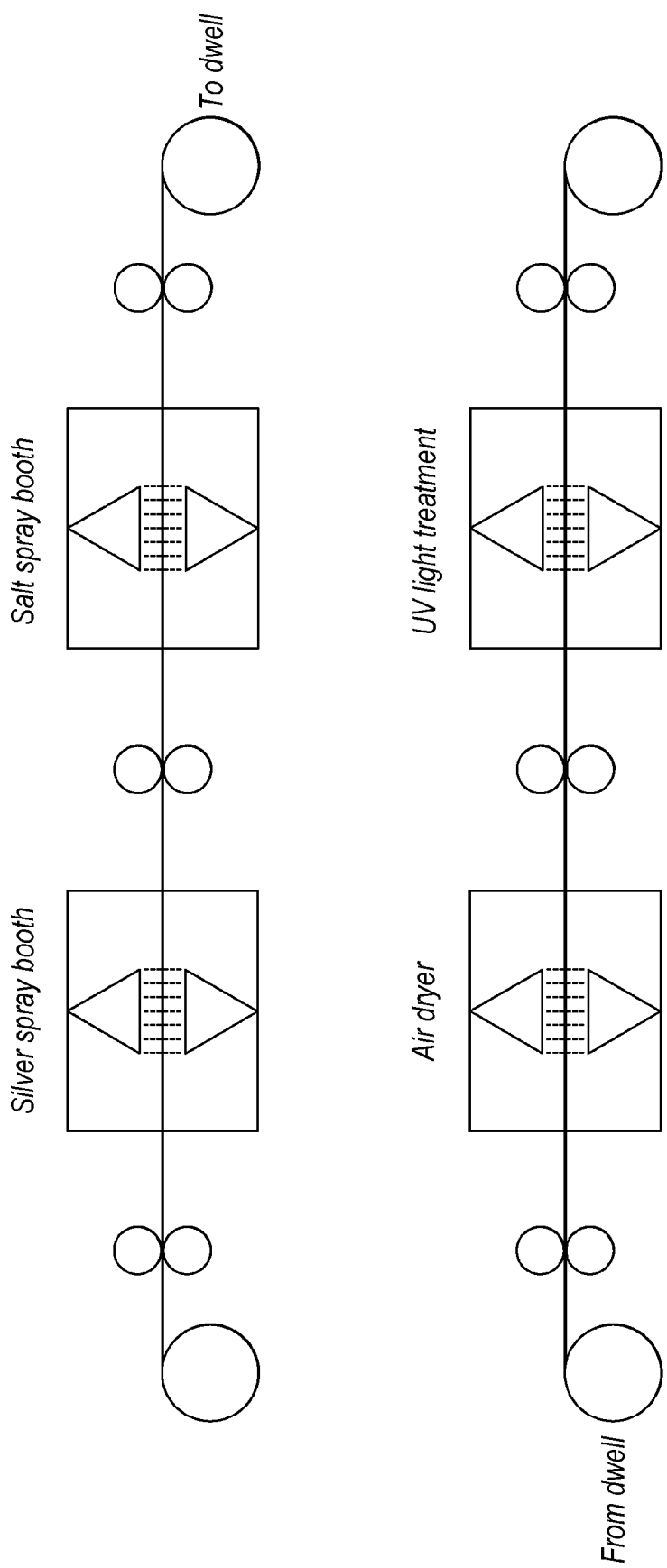
FIG. 5 shows a possible machine configuration used in the spray step of one embodiment of the process of the invention.

The spray coating process was carried out on the machinery arranged as shown in FIG. 5 using the process steps shown in the flow chart of FIG. 2. The fabric roll (weight up to 8 kg for 300 mm wide rolls and 16 kg for 600 mm wide rolls) was mounted on an unwind unit. The fabric passed from the unwind unit into a booth which contained the spray heads which were used to coat the fabric with a uniform coat weight of silver nitrate solution on both sides of the fabric. The fabric then passed into a second spray booth where it was sprayed with a sodium chloride solution to coat the fabric with a uniform coat weight on both sides of the fabric. The coating process roughly doubled the weight of the processed rolls.

Figure 3:
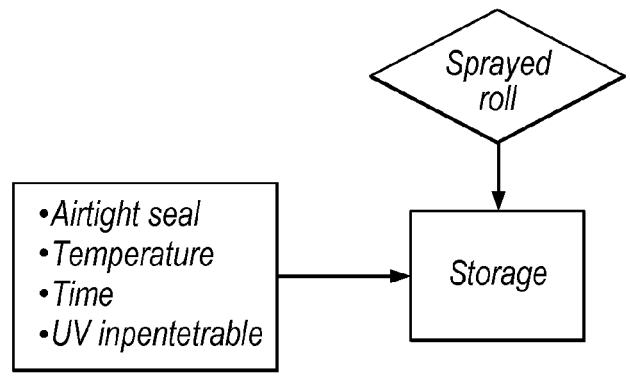
FIG. 3 shows a flow chart of the dwell step used in one embodiment of the process of the invention.

Once the fabric had been coated, the wet roll of fabric was placed in a plastic bag and kept in the dark for a specified period of time to allow a "curing" process to take place. Once this dwell period had elapsed, the wet roll of fabric was passed to the drying/UV treatment stage. The steps of this process are shown in the flow chart of FIG. 3. The fabric was held in the dwell stage for a period between 30 minutes and one hour.

Figure 4:
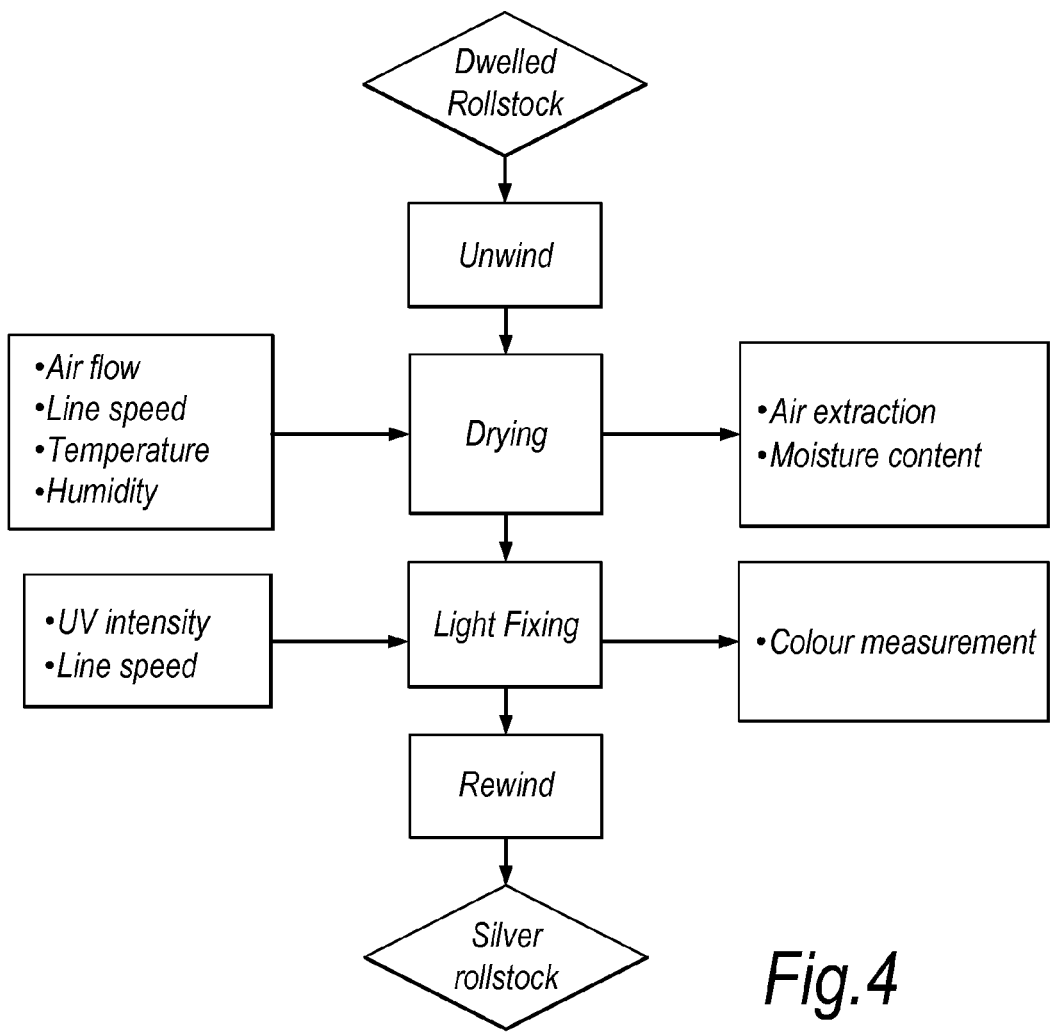
FIG. 4 shows a flow chart of the drying/light fixing step used in one embodiment of the process of the invention.

Once the fabric had been allowed to cure for the required time it was passed through a drying stage where the water was removed in an air stream from the fabric and it was dried to a constant water content. Dry fabric was then passed through a UV light treatment where it was exposed to UV light to generate a uniform grey appearance. Once the fabric had been allowed to develop a color it was wound on to package. These process steps are shown in the flow chart of FIG. 4.

The process above was carried out on a fabric of 55 to 80 grams per square meter basis weight using the process conditions of Table 1 resulting in the samples of Table 2.

TABLE 1

| Condition | Value |
| --- | --- |
| Line Speed | 2 m · min$^{-1}$ |
| Fabric width | 23 cm |
| Silver nitrate solution feed rate | 11 ml · min$^{-1}$ |
| Sodium chloride feed rate | 11 ml · min$^{-1}$ |

TABLE 2

| Sample | Aqueous Silver nitrate solution concentration % w/w | Aqueous sodium chloride solution concentration % w/w |
| --- | --- | --- |
| US 1 | 3% | 6% |
| US 2 | 3% | 6% |

EXAMPLE 2

The samples made in this example where manufactured by a similar process as that outlined in Example 1 except that the ultrasonic spray heads where replaced by conventional spray heads. The process conditions used are shown in Table 3 and the resulting samples in Table 4.

TABLE 3

| Condition | Value |
| --- | --- |
| Fabric width | 20 cm |
| Silver nitrate spray Compressed air feed | 55.2 kPa |
| Sodium chloride spray Compressed air feed | 55.2 kPa |

TABLE 4

| Sample | CS 1 | CS 2 | CS 3 | CS 4 | CS 5 | CS 6 |
| --- | --- | --- | --- | --- | --- | --- |
| Line speed in m · min$^{-1}$ | 1 | 2 | 3 | 1 | 1 | 1 |
| Aqueous silver nitrate solution concentration % w/w | 1.8 | 1.8 | 1.8 | 1.8 | 2.3 | 2.6 |
| Aqueous sodium chloride solution concentration % w/w | 6 | 6 | 6 | 7 | 7 | 7 |
| Silver nitrate solution feed rate ml · min$^{-1}$ | 8.5 | 17.5 | 30 | 8.5 | 8.5 | 8.5 |
| Sodium chloride feed rate in ml · min$^{-1}$ | 8.5 | 17.5 | 30 | 8.5 | 8.5 | 8.5 |

This process could only be operated for a short period of time before the heads blocked.

EXAMPLE 3

The ratio of silver to nitrate on a weight to weight basis found in the fabric produced by the process of the invention will be the same as that in the silver nitrate compound sprayed onto the precursor fabric as there are no other sources for either the silver or the nitrate ion and the sprayed fabric is not washed.

Silver nitrate is $AgNO_3$. The relative molecular mass of silver nitrate is 170 g/mol. The relative atomic mass of silver is 108 g/mol. The relative molecular mass of the nitrate ion is 62 g/mol. Hence, the w/w ratio of Silver to nitrate is 108/62=1.74.

The observed ratios for a fabric of the invention and Aquacel Ag (a carboxymethyl cellulose dressing that has been treated with a silver solution by rapid immersion) are given below. For each sample, the silver concentration present in the sample was measured by breaking down the sample in an acid digest. The resulting solution was measured against known silver standard solutions using atomic absorption spectroscopy. The nitrate concentration was measured by initially washing the samples in de-ionized water. The washings were diluted using de-ionized water. The samples were analyzed by ion chromatography using an ion exchange column in conjunction with an electrochemical detector against standard solutions of nitrate.

TABLE 5

| Material | % Ag w/w | % NO$_3$ w/w | Ag/NO$_3$ |
| --- | --- | --- | --- |
| Theoretical ratio on a dressing according to the invention | 1.20 | 0.69 | 1.74 |
| US2 | 1.28 | 0.84 | 1.53 |
| US2 | 1.00 | 0.30 | 3.34 |
| CS1 | 0.58 | 0.42 | 1.38 |
| CS2 | 0.51 | 0.38 | 1.33 |
| CS3 | 0.31 | 0.36 | 0.85 |
| CS4 | 1.30 | 0.80 | 1.63 |
| CS5 | 1.70 | 1.10 | 1.55 |
| CS6 | 2.20 | 1.10 | 2.00 |
| Average | | | 1.70 |
| Standard Deviation | | | 0.74 |

The theoretical ratio is calculated assuming that silver nitrate is sprayed onto the fabric and hence the ratio of silver to nitrate measured on the fabric is the same as that observed for the pure silver nitrate compound.

Samples of Aquacel Ag were analyzed as described above to determine the ratio of silver to nitrate in the dressing. The results are shown in Table 6.

TABLE 6

| Material Aquacel Ag Material lot number | % Ag w/w | % NO$_3$ w/w | Ag/NO$_3$ |
| --- | --- | --- | --- |
| 21756c | 1.24 | 0.14 | 8.72 |
| 3G65374 | 1.01 | 0.10 | 10.10 |
| 4A78987 | 0.96 | 0.10 | 9.60 |
| 4E85872 | 0.93 | 0.10 | 9.30 |
| 4E85880 | 1.00 | 0.10 | 10.00 |
| A4592 | 1.11 | 0.05 | 22.20 |
| 3E70203 | 0.97 | 0.10 | 9.70 |
| Average | | | 11.37 |
| Standard Deviation | | | 4.80 |

The theoretical ratio of silver to nitrate for a fabric according to the invention, sprayed with silver nitrate only is 1.74. The observed average ratio of silver to nitrate for the spray process as shown in the table above is 1.70 standard deviation 0.74.

The observed average ratio for a silvering process involving washing as used in the manufacture of Aquacel Ag is 11.37 standard deviation 4.8. The large difference is not due to the quantity of silver in the fabric according to the invention compared with Aquacel Ag, it is due to the nitrate level which in the fabrics according to the invention is higher because the fabrics are not washed. As illustrated in the following Example, the difference in nitrate content does not affect the essential antibacterial properties of the dressing according to the invention when compared to known antibacterial dressings.

EXAMPLE 4

Laboratory testing has shown the dissolution rate for silver from a fabric made by the process of the invention according to Example 1, but reinforced with nylon filaments, is similar to that for AQUACEL Ag (a carboxymethyl cellulose non-woven fabric with silver applied in a non-spray process) using the following method; 2 g of sample was placed in 200 ml of 0.9% (w/v) sodium chloride stirred at 37° C. Testing was carried out on three clinical trial batches of the dressing according to the invention. At selected time points (3 hrs, 24 hrs, etc), 10 ml was sampled and replaced with 10 ml of fresh dissolution medium. The samples were analyzed with an AA Spectrophotometer. A 1000 ppm silver standard was used. Figures show the rate of release (into saline) at each time point. Release is consistent over 160 hrs at approximately 0.4 ppm. Table 7 shows the rate of silver release from Aquacel Ag and the silver dressing of Example 1 reinforced with nylon.

TABLE 7

| Cell | Time (Hours) | | | | | |
|---|---|---|---|---|---|---|
| | 3 | 24 | 48 | 72 | 96 | 160 |
| Aquacel Ag-1 | 0.40 | 0.35 | 0.34 | 0.34 | 0.35 | 0.37 |
| Aquacel Ag-2 | 0.37 | 0.35 | 0.35 | 0.35 | 0.35 | 0.37 |
| Aquacel Ag-3 | 0.39 | 0.36 | 0.35 | 0.35 | 0.36 | 0.37 |
| Mean Aquacel Ag 1-3 | 0.39 | 0.35 | 0.35 | 0.35 | 0.35 | 0.37 |
| Ex 1 with nylon Cell-4 | 0.42 | 0.43 | 0.42 | 0.42 | 0.42 | 0.43 |
| Ex 1 with nylon Cell 5 | 0.42 | 0.42 | 0.41 | 0.42 | 0.42 | 0.43 |
| Ex 1 with nylon Cell-6 | 0.42 | 0.43 | 0.42 | 0.41 | 0.42 | 0.44 |
| Mean SHDRwN (Cell-4-6) | 0.42 | 0.43 | 0.42 | 0.42 | 0.42 | 0.43 |
| Ex 1 with nylon Cell-7 | 0.42 | 0.42 | 0.42 | 0.41 | 0.44 | 0.45 |
| Ex 1 with nylon Cell-8 | 0.41 | 0.42 | 0.42 | 0.42 | 0.42 | 0.45 |

TABLE 7-continued

| Cell | Time (Hours) | | | | | |
|---|---|---|---|---|---|---|
| | 3 | 24 | 48 | 72 | 96 | 160 |
| Ex 1 with nylon Cell-9 | 0.42 | 0.42 | 0.42 | 0.41 | 0.41 | 0.44 |
| Mean SHDRwN (Cell-7-9) | 0.42 | 0.42 | 0.42 | 0.41 | 0.42 | 0.45 |

We claim:

1. An antibacterial wound dressing comprising a silvered fabric comprising gel-forming fibers having silver ions linked thereto, the wound dressing having a final weight to weight ratio of silver to nitrate in the dressing of from 0.5 to 4 after drying, and a final amount of silver in the dressing of from 0.5% to 8% based on weight of the dressing.

2. The antibacterial wound dressing as claimed in claim 1 obtained by a process including the steps of:
   a. forming a fabric comprising gel forming fibers; and
   b. contacting the fabric with a solution containing silver nitrate by spraying the solution onto the fabric.

3. The antibacterial wound dressing as claimed in claim 2, wherein the fabric has two planar surfaces and is sprayed on both planar surfaces with the silver solution.

4. The antibacterial wound dressing as claimed in claim 2, wherein the fabric is in the form of a roll which is sprayed on opposite planes with said silver solution.

5. The antibacterial wound dressing as claimed in claim 2, wherein the spraying is carried out using an ultrasonic spray head to produce a spray in a fine mist.

6. The antibacterial wound dressing as claimed in claim 5, wherein the flow rate of solution delivered to the spray head is from 10 ml per minute to 100 ml per minute.

7. The antibacterial wound dressing as claimed in claim 2, wherein the solution comprises from 2% w/w to 10% w/w of silver nitrate in water.

8. The antibacterial wound dressing as claimed in claim 2, wherein the process comprises the additional step of spraying the fabric with a sodium chloride solution comprising from 5% w/w to 15% w/w of sodium chloride in water.

9. The antibacterial wound dressing as claimed in claim 8, wherein after the application of sodium chloride, the process comprises the additional steps of allowing the sprayed fabric to rest, drying the fabric and exposing the fabric to UV light.

* * * * *